United States Patent

Saneyoshi et al.

Patent Number: 6,121,248
Date of Patent: Sep. 19, 2000

[54] ANTI-VIRAL AGENT

[75] Inventors: Mineo Saneyoshi, Kanagawa; Toshiyuki Nagata, Ibaraki, both of Japan

[73] Assignee: Toagosei Co., Ltd., Tokyo, Japan

[21] Appl. No.: 09/146,133

[22] Filed: Sep. 2, 1998

[30] Foreign Application Priority Data

Apr. 1, 1998 [JP] Japan .................................. 10-105649

[51] Int. Cl.⁷ .................................................. A01N 43/04

[52] U.S. Cl. .............................. 514/49; 514/50; 536/27.4; 536/28.4; 536/28.52; 536/28.54

[58] Field of Search ............................... 536/27.4, 28.52, 536/28.55, 28.4; 514/49, 50

[56] References Cited

FOREIGN PATENT DOCUMENTS 9-31091  2/1997  Japan .

OTHER PUBLICATIONS

K. Feleczak et al, "Synthesis and Antitumour Properties of 2–Thio–5–Chloronucleosides", Nucleosides & Nucleotides, 14(3–5), 653–656 (1995).

M. Bretner et al, "Synthesis and Biological Activity of 5–Fluoro–2–Thiocytosine Nucleosides", Nucleosides & Nucleotides, 14(3–5), 657–660 (1995).

Jolanta M. Dzik et al, Synthesis and Interactions with Thymidylate Synthase of 2,4–Dithio Analogues of dUMP and 5–Fluoro–dUMP, Biochimica Et Biophysica Acta 1293 (1996) 1–8.

*Primary Examiner*—James O. Wilson
*Attorney, Agent, or Firm*—Oblon, Spivak, McClelland, Maier & Neustadt, P.C.

[57] ABSTRACT

Disclosed is an anti-viral agent against varicella-zoster virus or cytomegalovirus comprising, as an active ingredient, 2-thio-5-halogenopyrimidine arabinoside of the formula (1):

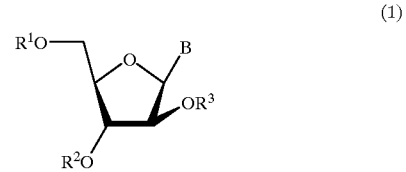

wherein B denotes a thiopyrimidine base of the formula (2) or (3):

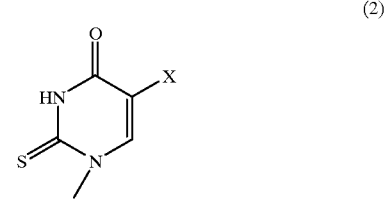

where X denotes a halogen atom; or

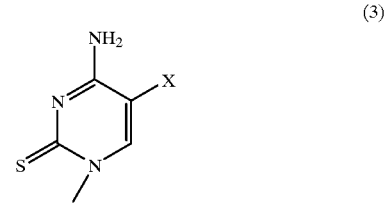

where X denotes a halogen atom; and
wherein each of $R^1$, $R^2$ and $R^3$ is a hydrogen atom or a hydroxyl protecting group.

8 Claims, 1 Drawing Sheet

ANTI-VIRAL AGENT

TECHNICAL FIELD

The present invention relates to an anti-viral agent comprising a particular nucleoside compound as an active ingredient. More specifically, it relates to an anti-viral agent against varicella-zoster virus or cytomegalovirus.

BACKGROUND ART

The highly effective and safe drugs against infections with herpesviruses have been developed extensively. Inter alia, acyclovir and vidarabine have been used for the treatment of infections with herpes simplex virus. However, there has not yet been found a compound having suitable efficacy and safety for treating infections with varicella-zoster virus and cytomegalovirus, which viruses also belong to the family herpesvirus.

DESCRIPTION OF THE INVENTION

The object of the present invention is to provide an anti-viral agent having a satisfactory efficacy, as well as safety, against varicella-zoster virus and cytomegalovirus.

We have intensively studied to solve the above-mentioned problem. As a result, we have now found that a particular type of nucleoside compounds had an effective anti-viral effect against both varicella-zoster virus and cytomegalovirus. The present invention has been achieved based on this finding. Thus, the present invention provides an anti-viral agent against varicella-zoster virus or cytomegalovirus comprising, as an active ingredient, 2-thio-5-halogenopyrimidine arabinoside of the formula (1):

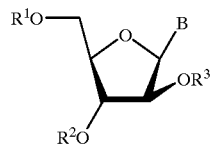

(1)

wherein B denotes a thiopyrimidine base of the formula (2) or (3):

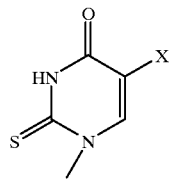

(2)

where X denotes a halogen atom; or

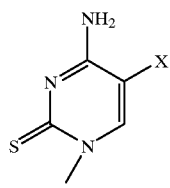

(3)

where X denotes a halogen atom; and wherein each of $R^1$, $R^2$ and $R^3$ is a hydrogen atom or a hydroxyl protecting group.

The 2-thio-5-halogenopyrimidine arabinoside of the present invention is a compound of the formula (1), wherein B denotes a thiopyrimidine base of the formula (2) or (3) and each of $R^1$, $R^2$ and $R^3$ is a hydrogen atom or a hydroxyl protecting group. Examples of the hydroxyl protecting group are acetyl, propionyl, butyroyl, isobutyroyl, pivaloyl, octanoyl, stearoyl, phenoxyacetyl, benzoyl, toluoyl, anisoyl, 4-chlorobenzoyl, ethoxycarbonyl, isopropoxycarbonyl, allyloxycarbonyl, phenoxycarbonyl, cinnamyloxycarbonyl, trityl, 4-methoxytrityl, 4,4'-dimethoxytrityl, trimethylsilyl, triethylsilyl, t-butyldimethylsilyl, t-butyldiphenylsilyl, tetrahydropyranyl and tetrahydrofuranyl groups, preferably acetyl, propionyl, butyroyl, isobutyroyl, pivaloyl, benzoyl, toluoyl, anisoyl, 4-chlorobenzoyl, trityl, 4-methoxytrityl, 4,4'-dimethoxytrityl and t-butyldimethylsilyl due to availability of materials.

In both the formulae (2) and (3), X denotes a halogen atom. Specifically, X is a fluorine, chlorine, bromine or iodine atom, preferably bromine or iodine atom in view of pharmacological activity.

Examples of the 2-thio-5-halogenopyrimidine arabinoside according to the present invention are 2-thio-5-fluorouracil arabinoside, 2-thio-5-chlorouracil arabinoside, 2-thio-5-bromouracil arabinoside, 2-thio-5-iodouracil arabinoside, 2-thio-5-fluorocytosine arabinoside, 2-thio-5-chlorocytosine arabinoside, 2-thio-5-bromocytosine arabinoside, and 2-thio-5-iodocytosine arabinoside.

Among the 2-thio-5-halogenopyrimidine arabinoside compounds according to the present invention, production of 2-thio-5-halogenouracil arabinoside, in which B of the formula (1) is a thiopyrimidine base of the formula (2), is described below.

First, 2-thiouracil arabinoside of the formula (4):

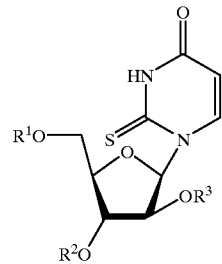

(4)

wherein each of $R^1$, $R^2$ and $R^3$ is a hydrogen atom or a hydroxyl protecting group is produced by the known method as described by W. V. Ruyle and T. Y. Shen, in J. Med. Chem., 10, 331 (1967) in combination with the introduction and conversion of protecting groups by conventional methods.

The 2-thiouracil arabinoside is then fluorinated, chlorinated, brominated or iodinated at the 5-position to give a corresponding 2-thio-5-halogenouracil arabinoside.

As another exemplary compound of the present invention, the 2-thio-5-halogenocytosine arabinoside in which B of the formula (1) is a thiopyrimidine base of the formula (3) can be produced in the following manner.

The above-obtained 2-thio-5-halogenouracil arabinoside is subjected to a reduction reaction according to a known method such as that described in W. V. Ruyle and T. Y. Shen, J. Med. Chem., 10, 331 (1967) or B. V. Joshi and C. B. Reese, C-V. N. S. Varaprasad, Nucleosides Nucleosides, 14, 209 (1995), to yield 2-thio-5-halogenocytosine arabinoside.

The 2-thio-5-halogenopyrimidine arabinoside of the present invention has an effective anti-viral activity against both varicella-zoster virus and cytomegalovirus, which viruses belong to the family Herpesvirus. Accordingly, therapeutic agents comprising the 2-thio-5-halogenopyrimidine arabinoside as an active ingredient are useful for the treatment of animals including human infected with each of the above viruses.

The therapeutic agent comprising the 2-thio-5-halogenopyrimidine arabinoside as an active ingredient can be administered through any route including oral, parenteral, enteral and topical administration routes. The dosage my be varied depending on patient's age or weight, type of diseases, severity, administration route, and so on, and may be determined appropriately while taking those factors into consideration.

In formulation, the 2-thio-5-halogenopyrimidine arabinoside may be used as a composition comprising a conventional pharmaceutical carrier, an excipient, and other additives. The dosage form may be of any type including tablets, granules, capsules, suppositories, injections, creams and sprays.

BEST MODES FOR CARRYING OUT THE INVENTION

Figure 1:
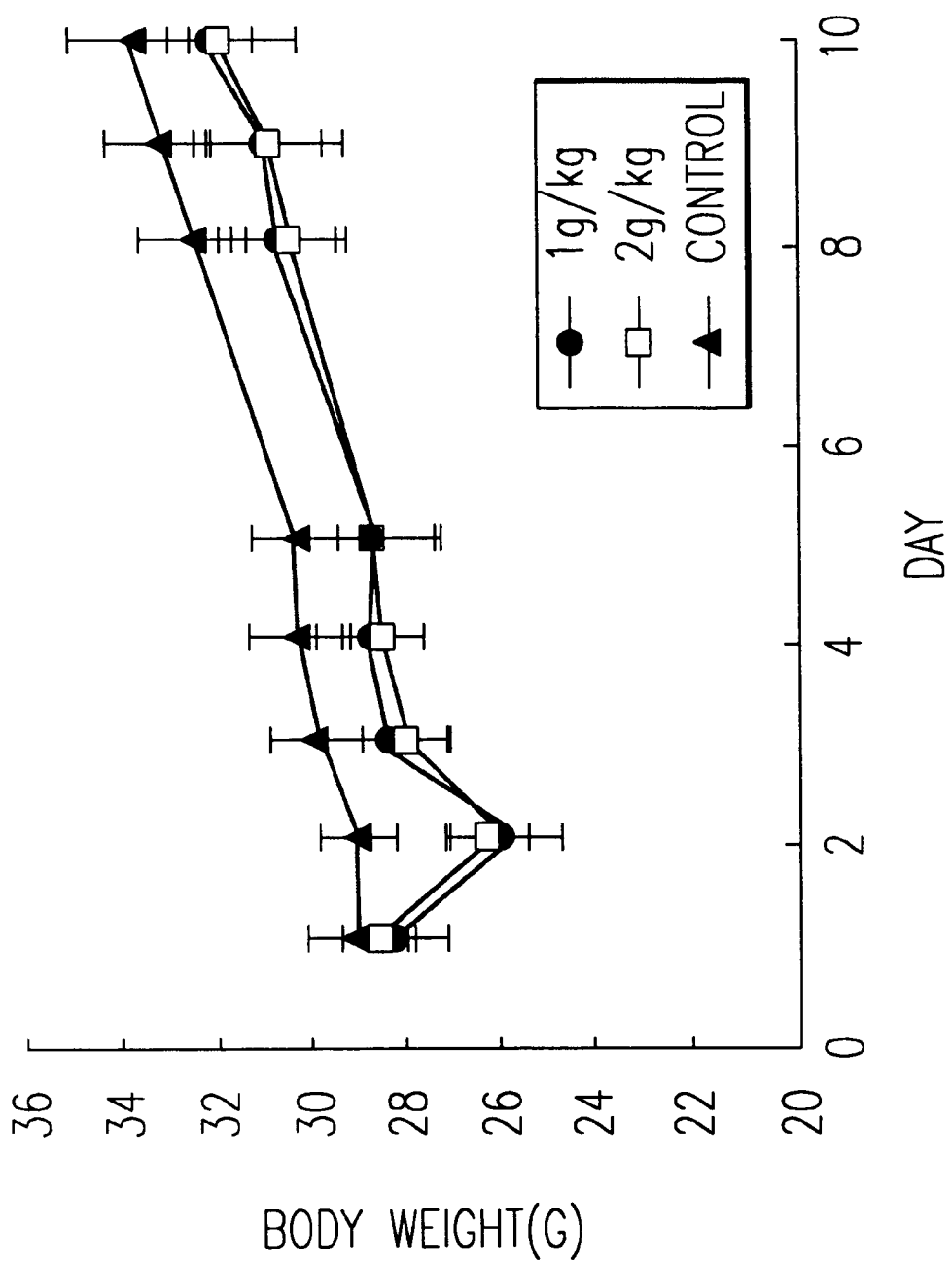
FIG. 1 shows the results of the acute toxicity test of 2-thio-5-iodocytosine arabinoside.

The present invention will be illustrated in more detail by the following examples. However, it should not be understood that the examples are intended to limit the invention.

EXAMPLE 1

Determination of Anti-viral Activity against Varicella-zoster Virus

The anti-viral activity against varicella-zoster virus was determined by the microplaque reduction method. That is, MRC-5 cells were cultured in a 96-well microtiter plate until the cells reached the confluent state. Each of the compounds being tested was added to the wells to which a preparation of varicella-zoster virus (HOSEN strain) was subsequently added. The plate was cultured at 35° C. in a $CO_2$ incubator. On day 3 after the culture, physiological saline containing 10% formalin was added to the wells and the plate was allowed to stand overnight to fix the cells to the wells. After wasing the plate, the cells were stained with a crystal violet solution and then washed. The focus formation by varicella-zoster virus was observed microscopically and the number of the foci was counted.

The concentration of each compound that inhibits by 50% of the number of foci observed in a group containing no compound was determined as a 50% effective density ($ED_{50}$).

The virus-free group in which, in place of the preparation of varicella-zoster virus, the culture medium was added to the MRC-5 cells was also cultured in the same manner. After staining, the cells were observed for their morphology to determine a 50% cytotoxic concentration ($CC_{50}$).

The selectivity index (SI), which is the ratio of the cytotoxic concentration to the anti-virally effective density, was determined by the equation:

$$SI = CC_{50}/ED_{50}$$

The results are shown in Table 1.

TABLE 1

| Anti-viral Activity against Varicella-zoster virus | | | |
|---|---|---|---|
| Compound | $ED_{50}$ ($\mu$g/ml) | $CC_{50}$ ($\mu$g/ml) | SI |
| 2-thio-5-iodouracil arabinoside | 3.1 | 20 | 6.5 |
| 2-thio-5-fluorocytosine arabinoside | 1.65 | >100 | >60 |
| 2-thio-5-bromocytosine arabinoside | 7.5 | >100 | >13 |
| 2-thio-5-iodocytosine arabinoside | 0.7 | >100 | >143 |

EXAMPLE 2

Determination of Anti-viral Activity against Cytomegalovirus

The anti-viral activity against cytomegalovirus was also determined by the microplaque reduction method in the same manner as in Example 1. That is, MRC-5 cells were cultured in a 96-well microtiter plate until the cells reached the confluent state. Each of the compounds being tested was added to the wells to which a preparation of human cytomegalovirus (AD 169 strain) was subsequently added. The plate was cultured at 37° C. in a $CO_2$ incubator. On day 6 after the culture, physiological saline containing 10% formalin was added to the wells and the plate was allowed to stand overnight to fix the cells to the wells. After washing the plate, the cells were stained with a crystal violet solution and then washed. The focus formation by cytomegalovirus was observed microscopically and the number of the foci was counted.

The concentration of each compound that inhibits by 50% of the number of foci observed in a group containing no compound was determined as a 50% effective density ($ED_{50}$).

The virus-free group in which, in place of the preparation of cytomegalovirus, the culture medium was added to the MRC-5 cells was also cultured in the same manner. After staining, the cells were observed for their morphology to determine a 50% cytotoxic concentration ($CC_{50}$).

The selectivity index (SI), which is the ratio of the cytotoxic concentration to the anti-virally effective density, was determined by the equation:

$$SI = CC_{50}/ED_{50}$$

The results are shown in Table 2.

TABLE 2

| Anti-viral Activity against Cytomegalovirus | | | |
|---|---|---|---|
| Compound | $ED_{50}$ ($\mu$g/ml) | $CC_{50}$ ($\mu$g/ml) | SI |
| 2-thio-5-fluorocytosine arabinoside | 0.16 | >100 | >625 |
| 2-thio-5-bromocytosine arabinoside | 2.4 | >100 | >42 |

TABLE 2-continued

Anti-viral Activity against Cytomegalovirus

| Compound | ED$_{50}$ (μg/ml) | CC$_{50}$ (μg/ml) | SI |
|---|---|---|---|
| 2-thio-5-iodocytosine arabinoside | 0.26 | >100 | >385 |

With respect to 2-thio-5-iodocytosine arabinoside (5-I-AraSC) which was evidenced to have the anti-viral effect in vitro, the acute toxicity was also determined in the following manner.

Mouse: ICR, male, 4 weeks;

Drug: 5-I-AraSC, 1 or 2 g/kg, ip., n=6.

The drug 5-I-AraSC was administered in a dosage of 1 or 2 g/kg to each mouse intraperitoneally, and the variation of a body weight of each mouse was examined.

As a result, there was a decrease in body weight by about 2 g in the mice administered with 5-I-AraSC on the day after administration. However, thereafter, the body weights of the administered mice varied in a similar way to that of the control mouse. No death of the mice was observed during the test (see Table 3 and FIG. 1). Accordingly, it can be said that the acute toxicity of 5-I-AraSC was not so strong.

TABLE 3

Results of Acute Toxicity Test

Variation of Body Weight

| Acute Toxicity | | 4/13 1 | 14 2 | 15 3 | 16 4 | 17 5 | 20 8 | 21 9 | 22 10 |
|---|---|---|---|---|---|---|---|---|---|
| 1 | 1 | 28.5 | 26.3 | 28.2 | 29.2 | 29.1 | 31.0 | 31.1 | 32.6 |
|  | 2 | 29.3 | 28.4 | 31.1 | 31.0 | 31.6 | 33.3 | 33.2 | 33.9 |
|  | 3 | 26.4 | 24.8 | 27.4 | 27.7 | 27.8 | 31.1 | 32.3 | 32.9 |
|  | 4 | 29.8 | 25.6 | 28.3 | 29.1 | 28.9 | 29.6 | 29.5 | 30.8 |
|  | 5 | 27.3 | 25.8 | 27.4 | 27.9 | 27.4 | 29.5 | 30.7 | 31.9 |
|  | 6 | 28.2 | 24.8 | 28.1 | 28.0 | 27.8 | 30.7 | 30.5 | 32.1 |
|  | Average | 28.3 | 26.0 | 28.4 | 28.8 | 28.8 | 30.9 | 31.2 | 32.4 |
|  | SD | 1.1 | 1.2 | 1.3 | 1.1 | 1.4 | 1.3 | 1.2 | 1.0 |
| 2 | 1 | 28.3 | 25.6 | 27.0 | 27.8 | 27.8 | 29.8 | 30.5 | 30.9 |
|  | 2 | 28.3 | 27.2 | 28.2 | 28.3 | 28.4 | 30.3 | 30.2 | 31.4 |
|  | 3 | 27.5 | 25.6 | 27.6 | 27.9 | 27.7 | 29.5 | 29.8 | 31.1 |
|  | 4 | 29.0 | 27.1 | 29.4 | 29.4 | 30.5 | 31.3 | 32.3 | 32.8 |
|  | 5 | 28.3 | 25.1 | 26.9 | 27.9 | 27.7 | 33.0 | 34.1 | 35.5 |
|  | 6 | 30.0 | 26.8 | 28.9 | 30.1 | 30.9 | 29.8 | 29.8 | 31.1 |
|  | Average | 28.6 | 26.2 | 28.0 | 28.6 | 28.8 | 30.6 | 31.1 | 32.1 |
|  | SD | 0.8 | 0.8 | 0.9 | 0.9 | 1.3 | 1.2 | 1.6 | 1.6 |
| 3 | 1 | 29.8 | 29.7 | 30.5 | 30.9 | 31.1 | 33.4 | 34.0 | 34.5 |
|  | 2 | 29.0 | 29.2 | 30.4 | 30.7 | 31.3 | 33.8 | 34.4 | 35.3 |
|  | 3 | 30.9 | 30.3 | 31.5 | 32.3 | 31.9 | 34.7 | 35.1 | 36.1 |
|  | 4 | 27.7 | 28.1 | 28.6 | 29.0 | 29.3 | 31.3 | 32.0 | 32.2 |
|  | 5 | 28.1 | 28.7 | 28.8 | 29.4 | 29.9 | 31.6 | 31.9 | 32.8 |
|  | 6 | 28.3 | 27.8 | 29.3 | 29.4 | 29.4 | 31.9 | 33.1 | 33.4 |
|  | 7 | 29.3 | 29.2 | 30.3 | 30.7 | 30.3 | 32.4 | 33.6 | 34.4 |
|  | Average | 29.0 | 29.0 | 29.9 | 30.3 | 30.5 | 32.7 | 33.4 | 34.1 |
|  | SD | 1.0 | 0.8 | 1.0 | 1.1 | 0.9 | 1.2 | 1.1 | 1.3 |

INDUSTRIAL APPLICABILITY

The anti-viral agent comprising, as an active ingredient, the 2-thio-5-halogenopyrimidine arabinoside according to the present invention has an anti-viral activity against both varicella-zoster virus and cytomegalovirus, and will therefore be useful in the fields of pharmaceuticals and nucleic acid chemistry.

What is claimed is:

1. An anti-varicella-zoster viral agent or anti-cytomegalovirus agent comprising, as an active ingredient, 2-thio-5-halogenopyrimidine arabinoside of the formula (1):

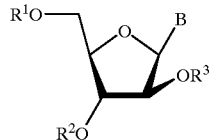

(1)

wherein B denotes a thiopyrimidine base of the formula (3)

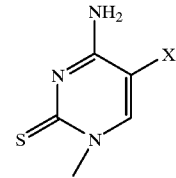

(3)

where X denotes a bromine or iodine atom; and wherein each of $R^1$, $R^2$ and $R^3$ is a hydrogen atom or a hydroxyl protecting group.

2. The anti-viral agent according to claim 1, wherein said 2-thio-5-halogenopyrimidine arabinoside is 2-thio-5-iodocytosine arabinoside or 2-thio-5-bromocytosine arabinoside.

3. An anti-viral agent against varicella-zoster virus or cytomegalovirus comprising 2-thio-5-iodocytosine arabinoside as an active ingredient.

4. A method for treating viral infections in an animal comprising administering to an animal in need thereof a compound represented by the formula (1):

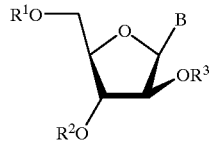

(1)

wherein B denotes a thiopyrimidine base of the formula (2) or (3):

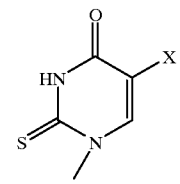

(2)

wherein X denotes a halogen atom; or

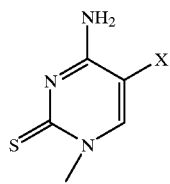 (3)

where X denotes a halogen atom; and
wherein each of $R^1$, $R^2$ and $R^3$ is a hydrogen atom or a hydroxyl protecting group.

5. The method of claim 4, wherein the viral infections are varicella-zoster virus infections.

6. The method of claim 4, wherein the viral infections are cytomegalovirus infections.

7. The method of claim 4, wherein said halogen atom in the formula (2) or (3) is a bromine or iodine atom.

8. The method of claim 4, wherein said B is a thiopyrimidine base of the formula (2) where the halogen atom is a bromine or iodine atom.

* * * * *